(12) United States Patent
Kanesaka

(10) Patent No.: US 6,340,364 B2
(45) Date of Patent: Jan. 22, 2002

(54) VASCULAR FILTERING DEVICE

(76) Inventor: Nozomu Kanesaka, 81 Greenwoods Rd., Old Tappan, NJ (US) 07675

( * ) Notice: Subject to any disclaimer, the term of this patent is extended or adjusted under 35 U.S.C. 154(b) by 0 days.

(21) Appl. No.: 09/769,312

(22) Filed: Jan. 26, 2001

Related U.S. Application Data

(63) Continuation-in-part of application No. 09/425,218, filed on Oct. 22, 1999.

(51) Int. Cl.$^7$ .............................................. A61M 29/00
(52) U.S. Cl. ...................................... 606/200; 606/198
(58) Field of Search ................................ 606/159, 198, 606/200; 604/96, 101

(56) References Cited

U.S. PATENT DOCUMENTS

| | | | | |
|---|---|---|---|---|
| 4,662,885 A | * | 5/1987 | Dipisa, Jr. et al. | 623/12 |
| 5,814,064 A | * | 9/1998 | Daniel et al. | 606/200 |
| 5,954,741 A | * | 9/1999 | Fox | 606/198 |
| 6,001,118 A | * | 12/1999 | Daniel et al. | 606/200 |
| 6,053,932 A | * | 4/2000 | Daniel et al. | 606/200 |

* cited by examiner

*Primary Examiner*—Gary Jackson
(74) *Attorney, Agent, or Firm*—Kanesaka & Takeuchi

(57) ABSTRACT

A vascular filtering device is formed of a flexible shaft having a passageway extending inside the shaft, an inflatable member communicating with the passageway and having a spiral form, and a filter member fixed to the distal end portion of the shaft. The inflatable member is attached at an inner side thereof to a distal end portion of the shaft. The filter member is attached to the shaft and fixed onto the outer side surface of the inflatable member along the entire length thereof. When the inflatable member is inflated, the filter member is enlarged to allow a blood containing debris or blood clots to flow through the filter member. Thus, the debris or blood clots are captured by the filter member. When the inflatable member is deflated, the filter member is disposed close to the side surface of the shaft. Thus, the filter member with the debris or clots can be easily removed from the blood vessel.

5 Claims, 1 Drawing Sheet

VASCULAR FILTERING DEVICE

CROSS REFERENCE TO RELATED APPLICATION

This is a continuation in part application of Ser. No. 09/425,218 filed on Oct. 22, 1999.

BACKGROUND OF THE INVENTION AND RELATED ART STATEMENT

The present invention relates to a device for capturing a debris or blood clots in a blood vessel, and more particularly, it relates to a vascular filtering device for capturing and removing the debris or blood clots used in, e.g. percutaneous transluminal coronary angioplasty (PTCA) procedure.

In recent years, an inter-vascular treatment, such as PTCA, has been widely practiced for a treatment of stenosis in the artery. In the PTCA procedure, a catheter which is provided with a balloon at a distal end thereof is inserted into a blood vessel which has a stenosis, and the balloon is inflated to enlarge the stenosis. Also, after enlarging the stenosis, a stent may be provided for preventing re-stenosis.

In performing the PTCA procedure, however, it may cause other problems. Namely, debris or blood clots formed at the stenosis may be separated from the portion at the stenosis and migrate to other critical area, such as brain and pulmonary arteries, while the PTCA procedure is being performed.

In order to remove the debris or blood clots while the PTCA procedure is being performed, a device having a mesh or net may be disposed in the blood vessel, as proposed in U.S. Pat. No. 6,001,118. The net is inflated by various inflating means to catch emboli, but the net with the emboli may not be smoothly removed from the blood vessel after use.

The present invention has been made in view of the above problem, and an object of the invention is to provide a vascular filtering device for removing debris or blood clots in the blood vessel of a patient during an operation, such as balloon dilation procedure.

Another object of the invention is to provide a vascular filtering device as stated above, which can be easily delivered to a desired location in the blood vessel and removed therefrom after capturing the debris or blood clots.

A further object of the invention is to provide a vascular filtering device as stated above, which is formed easily and is used as a guide wire or tube for other procedure.

Further objects and advantages of the invention will be apparent from the following description of the invention.

SUMMARY OF THE INVENTION

A vascular filtering device of the invention is basically formed of a flexible shaft, an inflatable member attached to the shaft, and a filter member attached to the inflatable member and the shaft.

The flexible shaft has a side surface, a passageway extending inside the flexible shaft, and a side opening formed in the side wall at a distal end portion of the shaft to communicate with the passageway. A fluid may be supplied to the passageway from a proximal end of the shaft.

The inflatable member has a spiral or helical form and is attached to the distal end portion of the shaft to communicate with the passageway through the side opening of the shaft. The inflatable member has an outer side surface, and an inner side surface entirely fixed to the side wall of the shaft not to be separated therefrom.

The filter member has a distal end sealingly fixed to the distal end portion of the shaft and an open end at a side opposite to the distal end. The filter member extends along the flexible shaft to cover the distal end portion thereof and is fixed onto the outer side surface of the inflatable member along an entire length thereof. Thus, when the inflatable member is inflated by providing the liquid to the inflatable member through the passageway, the filter member is enlarged to allow a foreign substance, such as blood clots and debris, to enter into the filter member through the open end to capture the same. When the inflatable member is deflated by forcibly removing the liquid from the inflatable member, the filter member with the blood clots and debris is closed or disposed close to the side surface of the shaft. Thus, the filtering device can be easily removed from the blood vessel.

When the filtering device of the invention is used, the inflatable member is made in a fully deflated condition. The distal end portion of the shaft is inserted into a blood vessel from a portion used in a regular PTCA procedure, and the shaft is advanced to a desired location in the blood vessel passing through a portion to be treated later. Then, a liquid is supplied to the inflatable member through the passageway to thereby inflate the inflatable member. Accordingly, the proximal end of the filter member is opened and is held between an inner wall of the blood vessel and the inflatable member. Blood in the blood vessel flows along the inflatable member and passes through the filter member to remove a foreign substance, such as debris and blood clots.

In this condition, since the filter and the inflatable member do not block the blood flow in the blood vessel, a required PTCA procedure can be made smoothly. If debris or blood clots is formed by the PTCA procedure and flows in the blood vessel, the debris or blood clots can be captures by the filter member.

After the PTCA procedure is finished, the inflatable member is deflated by forcibly removing the liquid in the inflatable member. Then, the filter member with the debris blood clots is removed from the blood vessel together with the shaft.

In the invention, since the inflatable member is attached to both shaft and filter member along the entire inner and outer portions, when the inflatable member is inflated, the filter member can surely abuts against the inner wall of the blood vessel. When the inflatable member is forcibly deflated, the filter member is disposed close to the outer surface of the shaft with the debris or blood clots therein. Thus, the shaft with the inflatable member and the filter member can be easily removed from the blood vessel. The debris or blood clots is removed smoothly together with the filter member.

Preferably, the shaft of the filtering device is used as a guide shaft for allowing a vascular treatment device to be transferred in a blood vessel, resulting in that the guide shaft has the filtering member for capturing a foreign substance formed in the vascular treatment procedure.

In the invention, the filtering device may be transferred in the blood vessel through a guide wire. In this case, the shaft includes a partition wall in the passageway, and a port in the side wall near the partition wall. The partition wall divides the passageway into a first passageway extending from the proximal end portion of the shaft to the opening to communicate with the inflatable member, and a second passageway extending from the port to the distal end of the shaft to allow the guide wire to pass therethrough. The filtering device can be transferred to a desired location easily and rapidly through the guide wire already disposed in the blood vessel, as in the balloon catheter system.

DETAILED DESCRIPTION OF PREFERRED EMBODIMENTS

Hereinafter, embodiments of a vascular filtering device of the present invention will be explained with reference to the attached drawings.

Figure 1:
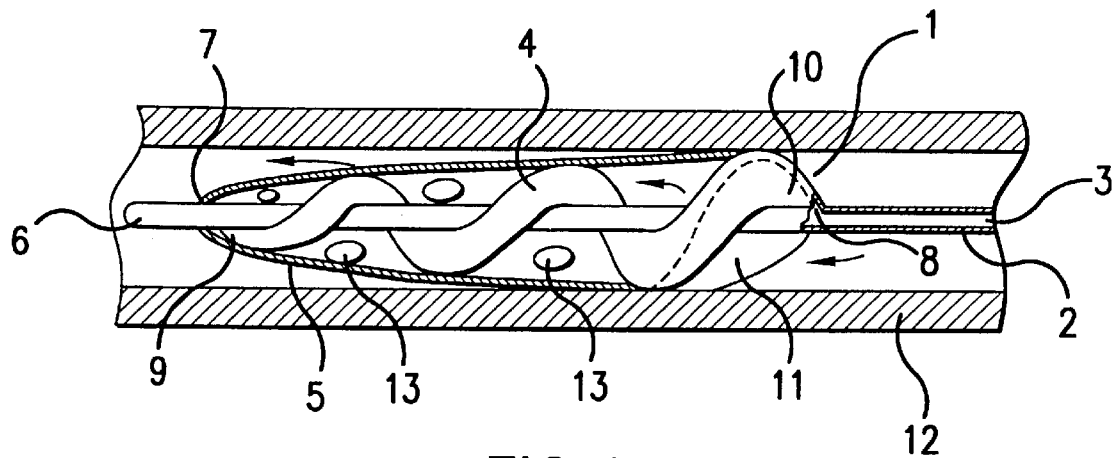
FIG. 1 is an explanatory view showing a first embodiment of a vascular filtering device of the invention placed in a blood vessel.

As shown in FIG. 1, a first embodiment of the vascular filtering device 1 is formed of a flexible shaft 2 having a passageway 3 therein, a tube-like balloon or inflatable member 4 helically wound around a distal end portion of the shaft 2, and a filter 5 in a substantially conical shape having a distal end 7 attached to the distal end of the shaft 2.

The shaft 2 may be made of metal or plastics, and has an elongated shape with flexibility to be inserted into a blood vessel, as in a regular PTCA device. In the first embodiment, the shaft 2 is used as a guide wire for a PTCA procedure.

The passageway 3 of the shaft 2 has an open end (not shown) at a proximal end of the shaft 2, and is closed at a distal end 6. The shaft 2 has an opening 8 on the side wall at the distal end portion of the shaft to communicate with an interior of the balloon 4 for inflating and deflating the balloon 4.

The balloon 4 is hollow and is spirally or helically wound around the shaft 2 from a front end 9 at the distal end 6 of the shaft 2 to a rear end 10 thereof. The diameter of the balloon 4 is gradually enlarged from the front end 9 to the rear end 10. Also, the balloon 4 is entirely fixed to the outer surface of the shaft 2 at the inner side thereof along the entire length of the balloon 4. There is no space between the balloon 4 and the shaft 2. Therefore, the distance from the outer side of the balloon to the outer surface of the shaft 2 gradually increases from the front end 9 to the rear end 10.

The rear end 10 of the balloon 4 is sealingly connected to the opening 8 of the shaft 2, so that the passageway 3 communicates with the interior of the balloon 4. The front end 9 may also be communicated with the passageway 3.

Incidentally, the vascular filtering device 1 shown in FIG. 1 is in a condition that the balloon 4 is inflated in the blood vessel.

The filter 5 shown in section in FIG. 1 surrounds the helically wound balloon 4, and is fixed to the entire outside surface of the balloon 4. Therefore, when the balloon 4 is inflated, the filter 5 mounted on the balloon 4 is expanded to form the conical shape as shown in FIG. 1. Also, when the balloon 4 is deflated, the filter 5 attached to the balloon 4 is disposed close to the outer surface of the shaft 2.

A bottom or enlarged portion of the conical shape filter 5 is opened to have an opening 11 shown in the figure, and a periphery of the opening 8 is partly attached to the balloon 4. The filter 5 has a thickness of about 0.254 mm (0.001 inch) to 0.508 mm (0.002 inch), and includes numerous pores for allowing liquid, such as blood, to pass therethrough. The diameter of each pore is approximately 6 $\mu$m such that certain undesired substances, such as debris or blood clots, can not pass through the pores of the filter 5 while red and white blood corpuscles and so on can pass therethrough.

In use, the vascular filtering device 1 structured as described above is prepared such that the balloon 4 and the filter 5 are collapsed. In this condition, the filtering device 1 is entered into a blood vessel, e.g. vein of a foot, similar to installing a guide wire into the blood vessel. The shaft is advanced, and the balloon 4 at the distal end portion of the shaft 2 passes through a treatment portion, e.g. stenosis, by a PTCA procedure later operated. Then, a liquid is supplied to the balloon 4 through the passageway 3 to inflate the balloon 4 to set the shaft. As a result, the filter 5 is opened and is held between an inner wall of a blood vessel 12 and the balloon 4. Thus, the filter 5 is set at a downstream of the blood vessel 12 relative to the treatment portion. In this condition, since the blood flows along the path around the balloon 4 and passes through the filter 5, this condition is kept until the required operation, e.g. PTCA procedure for opening stenosis and installing a stent, is completed.

In case debris or blood clots 13 occurs at the upstream side of the blood vessel 12 during the PTCA procedure, blood containing the debris or blood clots 13 flows to the downstream of the blood vessel 12 in a direction shown by arrows in FIG. 1. Blood containing debris or blood clots 13 flows into the opening 11 of the filter 5, and flows along the helical path of the balloon 4. Blood passes through the pores of the filter 5, while the debris or blood clots 13 is caught inside the conical shaped filter 5 since they can not pass through the pores of the filter 5.

After the PTCA procedure is completed, the balloon 4 is deflated to collapse the filter 5 containing the debris or blood clots 13 therein by forcibly removing the liquid inside the balloon 4. Since the filter 5 is fixed to the outer surface of the balloon 4, when the balloon 4 is deflated, the filter 5 is also collapsed and disposed close to the shaft 2 while the debris or blood clots 13 are held between the filter and the shaft 2. Then, the vascular filtering device 1 is removed from the blood vessel 12 by pulling the vascular filtering device 1 in a direction opposite to the direction of the blood flow. Accordingly, the debris or blood clots 13 formed at the PTCA procedure can be removed from the blood vessel 12.

In the invention, when the balloon 4 is deflated, the filter 5 is collapsed to be located close to the outer surface of the shaft 2. Therefore, although the debris or blood clots 13 is caught by the filter 5, the size of the filter 5 is made small. Thus, the filtering device 1 of the invention can be removed from the blood vessel 12 smoothly.

Figure 2:
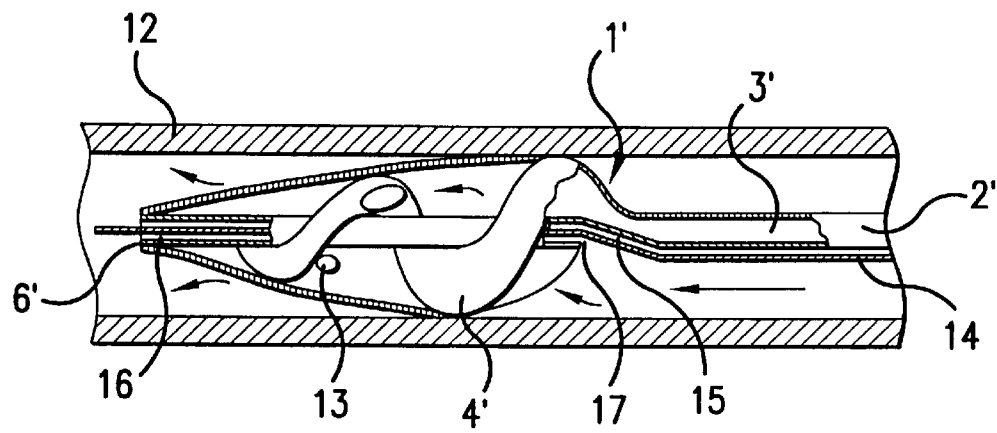
FIG. 2 is an explanatory view showing a second embodiment of a vascular filtering device of the invention placed in a blood vessel.

FIG. 2 shows a second embodiment of the vascular filtering device 1' of the invention. The vascular filtering device 1' is designed to be delivered to the proper position in the blood vessel through a guide wire 14 already placed in the blood vessel, and has a rapid exchange system.

Namely, in the filtering device 1', a shaft 2' has a partition wall 15 therein to divide a passageway into an inflation passageway 3' for inflating a balloon 4' and a guidewire passageway 16. Also, a guidewire port 17 is provided near the partition wall 15 of the shaft, and the shaft 2' has an opening 6' at a distal end thereof. The guide wire 14 can pass through the guidewire port 17, the passageway 15 and the opening 6'. In the vascular filtering device 1', the balloon 4' has an elongated spiral shape slightly shorter than that of the balloon 4, and is communicated with the passageway 3' at one portion.

In use, an end of the guide wire 14 is inserted into the passageway 15, and the vascular filtering device 1' is pushed into the blood vessel 12 along the guide wire 14. After the filtering device 1' is disposed in the proper position, the balloon 4' is inflated to open and set the filter 5. Then, the required operation is carried out, and if debris or blood clots 13 is formed, it is captured by the filter 5. In this embodiment, in case the vascular filtering device 1' is to be exchanged, the vascular filtering device 1' can be removed from the blood vessel 12 over the guide wire 14 while the guide wire 14 is left in the blood vessel 12. Thereafter, another vascular filtering device 1' can be introduced in the blood vessel 12 over the guide wire 14.

According to the present invention, since the vascular filtering device having a filter at a distal end portion thereof can be placed in the downstream of the blood vessel while a PTCA procedure is operated in an upstream of the blood vessel, even if blood containing blood clots or debris due to PTCA procedure flows to the downstream of the blood vessel, the blood clots or debris can be captured and removed by the vascular filtering device without blocking the blood flow. Thus, the debris or blood clots can be prevented from migrating to the critical area, such as brain and pulmonary arteries, during and after the PTCA procedure.

In the invention, since the balloon is firmly fixed to the shaft and the filter at the inner and outer portions thereof, the filter can be surely located in the blood vessel in use, and also, the filter with the debris or blood clots can be made compact on the shaft to be easily removed from the blood vessel.

While the invention has been explained with reference to the specific embodiments of the invention, the explanation is illustrative and the invention is limited only by the appended claims.

What is claimed is:

1. A vascular filtering device, comprising:
   a flexible shaft having a side surface, a passageway extending inside the flexible shaft, and a side opening formed in the side surface at a distal end portion of the shaft and communicating with the passageway,
   an inflatable member having a spiral form and attached to the distal end portion of the shaft to communicate with the passageway through the side opening of the shaft, said inflatable member having an outer side surface, and an inner side surface entirely fixed to the side wall of the shaft, and
   a filter member having a distal end sealingly fixed to the distal end portion of the shaft and an open end at a side opposite to the distal end thereof, said filter member extending along the flexible shaft and fixed onto the outer side surface of the inflatable member along an entire length thereof so that when the inflatable member is inflated, the filter member is enlarged to allow a foreign substance to enter into the filter member through the open end, and when the inflatable member is deflated, the filter member is disposed close to the side surface of the shaft.

2. A vascular filtering device according to claim 1, wherein said shaft is a guide shaft for allowing a vascular treatment device to be transferred in a blood vessel.

3. A vascular filtering device according to claim 1, wherein said filter member has a bag shape opening toward a proximal end portion of the shaft.

4. A vascular filtering device according to claim 1, wherein said inflatable member has a tubular shape with a hollow portion therein extending substantially throughout an entire length thereof, said hollow portion having a diameter gradually enlarging from the distal end of the shaft.

5. A vascular filtering device according to claim 1, wherein said shaft includes a partition wall therein, and a port in the side wall near the partition wall, said partition wall dividing the passageway into a first passageway extending from a proximal end portion of the shaft to the opening to communicate with the inflatable member, and a second passageway extending from the port to a distal end of the shaft to allow a guide wire to pass therethrough.

* * * * *